United States Patent [19]

Sanford et al.

[11] Patent Number: 4,933,274
[45] Date of Patent: Jun. 12, 1990

[54] PROCESS FOR DETECTING GENETIC SUSCEPTIBILITY TO CANCER

[75] Inventors: Katherine K. Sanford, Dover, Del.; Ram Parshad, Silver Spring; Gary M. Jones, Ijamsville, both of Md.

[73] Assignee: United States of America Represented by the Secretary of the Department of Health and Human Services, Washington, D.C.

[21] Appl. No.: 270,030

[22] Filed: Nov. 14, 1988

[51] Int. Cl.$^5$ .............................................. G01N 33/48
[52] U.S. Cl. ........................................ 435/6; 435/29; 435/34; 436/63; 436/64; 436/813
[58] Field of Search ......................... 436/63, 64, 813; 435/29, 34, 240.21, 6; 424/3, 7.1

[56] References Cited

PUBLICATIONS

Allen, J. W.; Brock, K.; Campbell J., Shariff Y.; "Sister Chromatid Exchange Analysis in Lymphocytes" in *Single–Cell Mutation Monitoring Systems*, Ansari, A. A. and De Seres, F. J., eds., Plenum Press, N.Y. and London, pp. 145–163.

Obe, G., Beek, B., "The Human Leukocyte Test System" in *Chemical Mutagens Principles & Methods for Their Detection*, de Serres, F. J., & Hollaender, A., eds., Plenum Press, N.Y. and London, (1982), pp. 386–391.

Priest, Jean H., M.D.; "Medical Cytogenetics and Cell Culture" 268–269, pp. 60, 61, 102–107, 130–131, 292, 293, 296, 297, 298–303, 320–321, 324–327, Leu & Febiger (1977), Philadelphia.

Preston, J., "Cytogenic Abnormalities as an Indicator of Mutagenic Exposure" in *Single-Cell Mutation Monitoring Systems*, Ansari, A. A. and De Seres, F. J., eds., Plenum Press, N.Y. and London, pp. 127–143.

Mitchell, A. D.; Mirsalis, J. C.; "Unscheduled DNA Synthesis as an Indicator of Genotoxic Exposure" in *Single-Cell Mutation Monitoring Systems*, Ansari, A. A. and De Seres, F. J., eds., Plenum Press, NY and London, pp. 180–182.

Carrano, A. V.; Moore, II, D. H.; "The Rationale and Methodology for Quantifying Sister Chromatid Exchange in Humans" in *Mutagenicity–New Horizons in Genetic Toxicology*, Heddle, J. A., ed., Academic Press (1982), pp. 268–273.

Risley, M. S., "Mitotic Chromosomes", in *Advanced Cell Biology*, Schwartz, L. M. and Azar, M. M., eds., Van Nostrand Reinhold Company, (1981), pp. 1056–1059.

Penso, G.; Verani, P.; and Balducci, D.; "Nuclear Abnormalities in Irradiated Cultures: Relationship with those Reported in Virus Transformed Cells", in *Cancer Cells in Culture*, Katsuta, H., ed., University of Tokyo Press, (1968), pp. 205–215.

*Primary Examiner*—Christine M. Nucker
*Attorney, Agent, or Firm*—Cushman, Darby & Cushman

[57] ABSTRACT

A process for determining genetic susceptibility to cancer is disclosed in which the frequency of chromatid breaks and gaps is calculated in metaphase skin fibroblasts or stimulated peripheral blood lymphocytes after x-irradiation or fluorescent light exposure. Susceptibility to cancer is found when the frequency of breaks and gaps in the cell sample is two to three-fold higher than that occurring in comparable cells from control individuals. Various factors have been found which influence the accuracy of the test results. These factors include pH, temperature, cell density, culture medium or serum, microbial contamination and visible light exposure (effective wavelength 500 nm). Additionally, because of experimental variability, known normal controls are suggested for use in each test group.

11 Claims, 7 Drawing Sheets

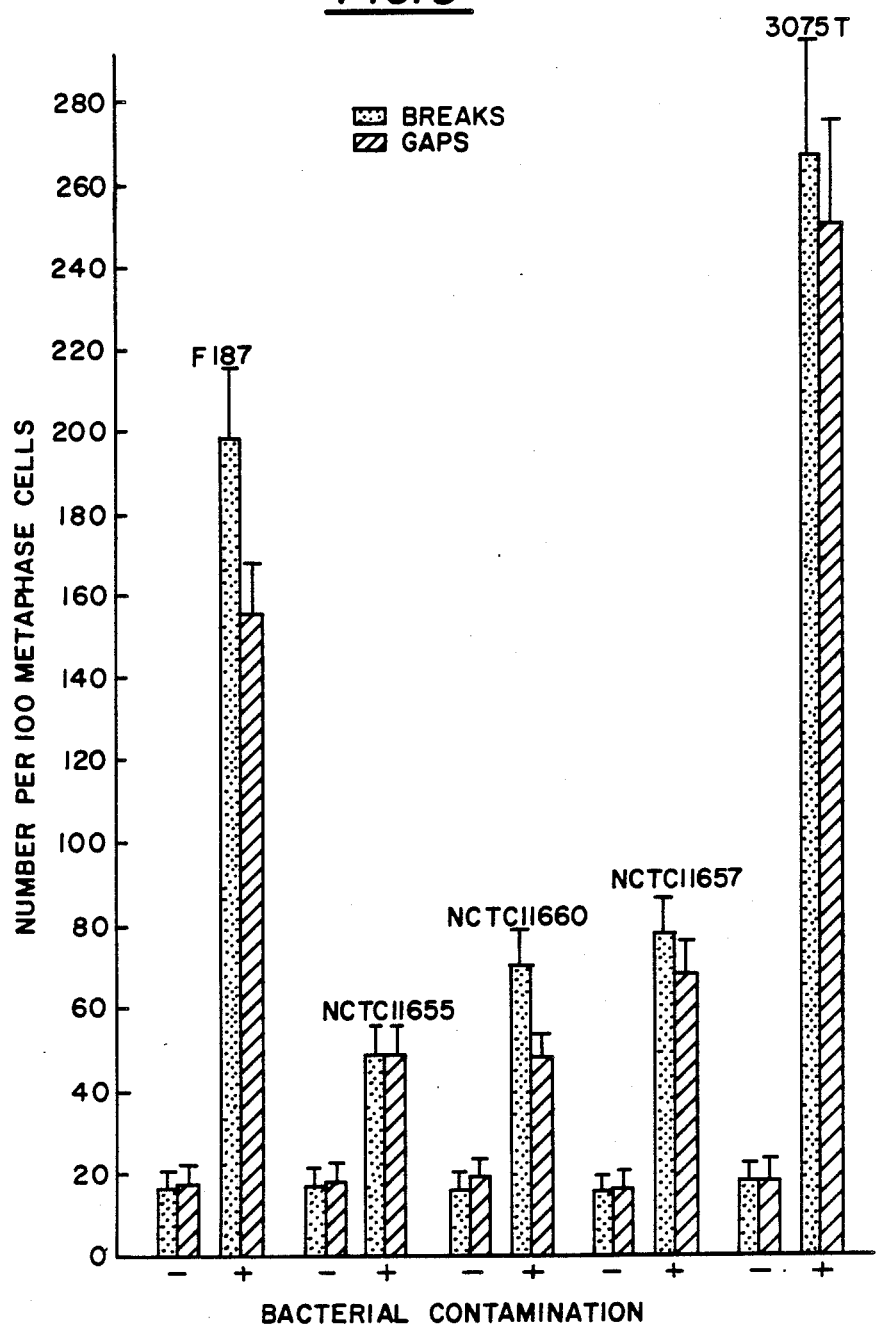

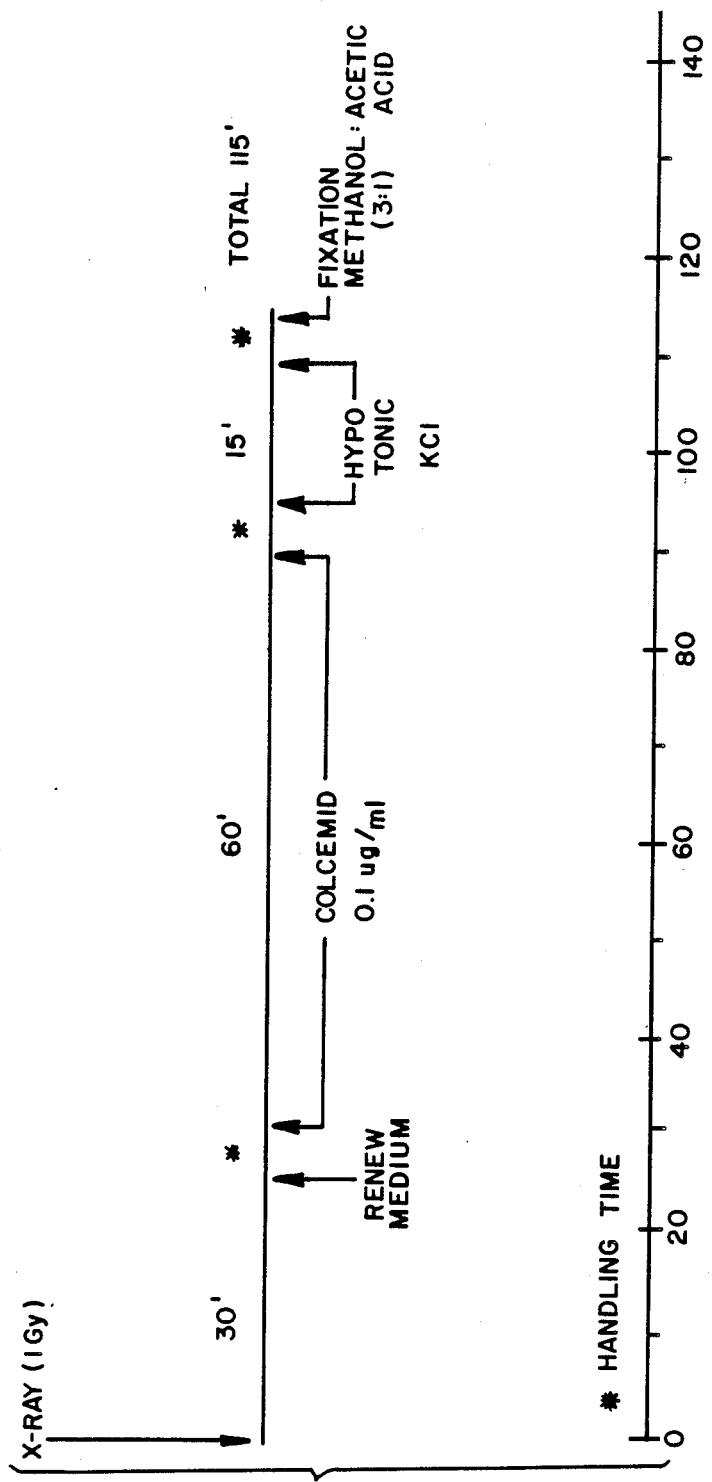

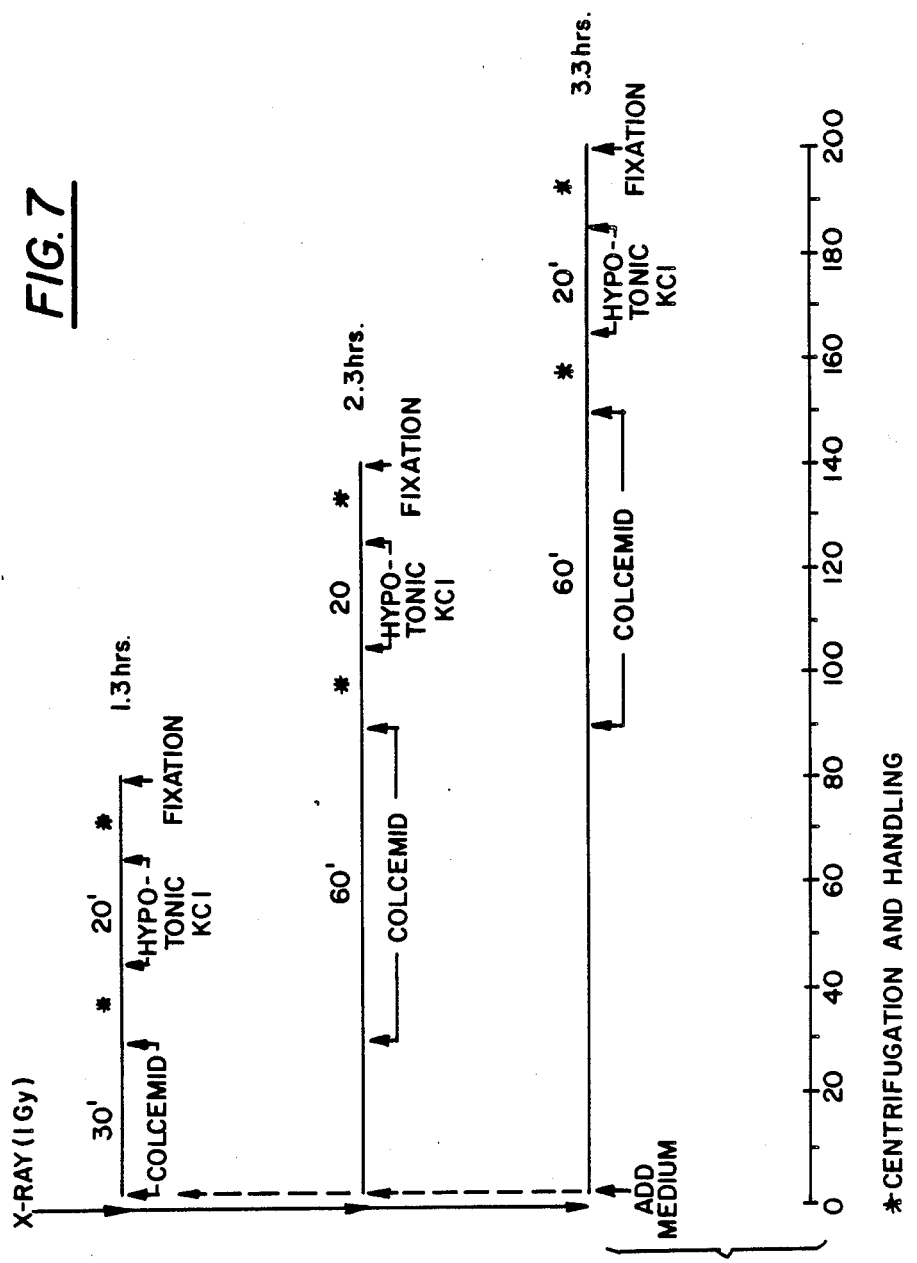

PROCESS FOR DETECTING GENETIC SUSCEPTIBILITY TO CANCER

BACKGROUND OF THE INVENTION

A group of genetic disorders with widely different clinical manifestations predispose affected individuals to a high risk of cancer. Four of these disorders are rare, recessively transmitted traits, they are: ataxia telangiectasia (A-T), Fanconi anemia (FA), Bloom syndrome and xeroderma pigmentosum (XP). The first three disorders are collectively called chromosome-breakage syndromes, and they share the characteristic of chromosome instability, while the fourth disorder, XP, is characterized by high sensitivity to sun exposure and susceptibility to skin cancer. Skin fibroblasts or blood lymphocytes from individuals with these disorders show increased sensitivity to mutagens and DNA-damaging agents, suggestive of defects in DNA repair; such a defect has, in fact, been established in XP.

In addition to these rare disorders, certain neoplasms are also hereditary with distinct patterns of Mendelian behavior in man. Five of these disorders, namely, familial polyposis, Gardner syndrome, retinoblastoma, Wilms'tumor and hereditary cutaneous malignant melanoma (HCMM) (with its precursor lesion, the dysplastic nevus) are inherited as autosomal dominant traits. These tumors occur less commonly in the hereditary than the nonhereditary form, tend to develop earlier in life and to arise from multiple foci. In addition to these dominantly inherited neoplasms, there are numerous other cancers which tend to occur in clusters with a familial tendency (see e.g., Fraumeni, J.D. Jr. "Clinical Patterns of Familial Cancer". Chaganti et al. (eds.), *Genetics in Clinical Oncology*, pp. 223-233 (New York: Oxford University Press (1977)).

In examining skin fibroblasts from individuals with hereditary tumors or familial cancers, a common abnormality in their response to irradiation has been observed during the $G_2$ phase of the cell cycle. Exposure to X-rays (100R) or cool-white fluorescent light (8 W/M$^2$) produces chromatid breaks and gaps observable in the first post-treatment metaphase. The frequencies of these aberrations have been found by the present inventors to be several-fold higher in skin fibroblasts from individuals in whose families the previous disorders are present (genetically predisposed individuals), than in comparable cells taken from clinically normal (control) individuals. Similar observations have also been reported with respect to skin fibroblasts and peripheral blood lymphocytes from individuals with A-T or FA (see e.g., Rary et al. "Cytogenetic Studies of Ataxia Telangiectasia". Am. J. Human Genet., 26:70A (1974); Taylor, A.M.R. "Unrepaired DNA Strand Breaks in Irradiated Ataxia Telangiectasia Lymphocytes Suggested from Cytogenetic Observations". Mutat. Res., 50:407-418 (1978); Bigelow et al. "$G_2$ Chromosomal Radiosensitivity in Fanconi's Anemia". Mutat. Res., 63:189-199 (1979); and Natarajan et al. "Chromosomal Radiosensitivity of Ataxia Telangiectasia Cells at Different Cell Cycle Stages". Hum. Genet., 52:127-132 (1979)). Additionally, cultures of human blood lymphocytes taken from cancer patients, including many with hereditary cancers, and treated during $G_2$ phase with the radiomimetic chemical bleomycin generally showed a higher frequency of chemically-induced chromatid damage than comparable cells from healthy, normal donors (Hsu et al. "Differential Mutagen Susceptibility in Cultured Lymphocytes of Normal Individuals and Cancer Patients". Cancer Genet. Cytogenet. 17:307-313 (1985)).

The inventors have observed this abnormal response to $G_2$ irradiation in all the human tumor cells they examined, irrespective of histopathology or tissue origin. The same response has also been seen in human keratinocytes in culture prior to neoplastic transformation. In somatic cell hybrids produced by fusion of a normal skin fibroblast with a tumor cell, HeLa, the enhanced chromosomal radiosensitivity was suppressed and segregated with the tumorigenic phenotype. Cytogenetic and biochemical studies with and without DNA repair inhibitors suggest that the enhanced chromatid damage seen during the post-irradiation period results from deficient DNA repair processes during $G_2$.

From the observations and results discussed above, it was theorized by the inventors that based on the magnitude of the chromatid damage which resulted from exposure of cells in culture to X-rays or visible light, and the association of such damage with genetic disorders predisposing an individual to cancer or hereditary neoplasms, a quantitative assay for determining genetic predisposition or susceptibility to cancer could be developed. The inventors believed that an accurate and reproducible assay could be formulated based on the observation that the phenotype associated with cancer predisposition appears to result from deficient DNA repair processes during $G_2$ phase. This repair deficiency(ies) would lead to genetic instability which, in turn, would increase the probability of mutations such as inactivation or loss of the normal allele at a heterozygous cancer-predisposing locus. Thus, the inventors endeavored to develop a quantitative assay for identifying cancer susceptibility, and, further in that regard, to determine what assay parameters would affect the cellular responses to X-irradiation in such a way as to produce false positives.

SUMMARY OF INVENTION

Cancer-prone genetic disorders and hereditary familial neoplasms are not common. However, an unknown, possibly sizable, fraction of the general population must be carriers of the mutant genes for the $G_2$ repair deficiency. Ataxia telangiectasia heterozygotes alone are reported to comprise about 2.8% of the general population or about 7 million persons in the United States. These individuals are at high cancer risk; they also can transmit the mutant genes to future generations. Their detection is thus of fundamental importance for the prevention and control of cancer. Within families having a known cancer-prone genetic disorder or neoplastic disease such as A-T or HCMM/DNS, an assay for $G_2$ deficiency can detect clinically normal carriers of the mutant disease gene and those individuals who have the mutant gene in either homozygous or heterozygous form even before appearance of clinical symptoms. Although the $G_2$ response and assay cannot identify, at the present time, a particular cancer-prone mutant disease, it can provide a procedure with which to screen the general population for individuals genetically predisposed to cancer and thus at high cancer risk.

The present invention provides an assay for detecting predisposition or susceptibility to cancer. The invention comprises an assay and a kit formed therewith, with which to test for cancer susceptibility by statistical comparison of chromatid break and gap frequency arising in a test skin fibroblast sample with that occurring in the comparable control.

According to the present invention, log phase skin fibroblasts (protected at all times from light of wavelength <500 nm) are prepared using both normal (control) cells and cells from an individual to be tested for predisposition to cancer. These cells are then x-irradiated at approximately 126 R per minute or exposed to cool-white fluorescent light (e.g. $8W/M^2$). After irradiation the cultures are incubated to allow the cells in metaphase at the time of irradiation to proceed to $G_1$, so as to be excluded from further analysis. The cultures are then treated with Colcemid (N-desacetyl-N-methylcolchicine) and incubated to to arrest cell division and thus accumulate the cells entering metaphase. The samples are fixed, air-dried, stained and mounted for scoring.

To quantify chromatid damage in both the test and control samples, 50 to 100 metaphase cells from each culture are examined for chromatid breaks and gaps. Chromatid interchanges generally do not occur for they arise infrequently in human fibroblasts. Breaks appear as chromatid discontinuities with displacement of the broken segment, while gaps (non-staining regions) show no displacement of the segment distal to the lesion. Gaps are scored only if they are longer than the chromatid width (see, ISCN: An International System for Human Cytogenetic Nomenclature. Cytogenet. Cell Genet., 21:309–404 (1978)). Cells in prometaphase or metaphase cells with understained or overstained chromosomes are not considered suitable for analysis because understained chromosomes could have unstained gap-like regions, while overstaining could obscure gaps.

To ensure accuracy and reproducibility of results in the present process, various process parameters merit particular consideration and control samples should always be run. The parameters include: pH, temperature, cell density, culture medium or serum, microbial contamination and visible light exposure (effective wavelength 405 nm). These are each discussed in more detail below.

DETAILED DESCRIPTION OF THE INVENTION

The following is exemplary of the present process and incorporates suitable process parameters for use herein. These parameters may be varied, however, and the following should not be deemed limiting of the present claims.

MATERIALS AND METHODS

Source of cells. Cultures of skin fibroblasts developed from biopsy material as described for example by Goetz, I.E. "Growth of human skin fibroblasts from punch biopsies". TCA Manual, 1:13:15 (1975), Tissue Culture Methods and Applications, P.F. Kruse, Jr. and M.K. Patterson, Jr. Eds., Academic Press, New York, 1973) and established cell lines obtained from cell repositories such as the American Type Culture Collection, 12301 Parklawn Drive, Rockville, MD 20852 or NIGMS Human Genetic Mutant Cell Repository, Coriell Institute of Medical Research, Copewood and Davis Streets, Camden, N.J. 08103 may be used. For instance, in the examples described below various lines of skin fibroblasts were obtained from the NIGMS Human Genetic Mutant Cell Repository (GM) and the NIH Aging Cell Repository (AS and IMR 90). Other cell lines used herein were gifts donated by Drs. Y Shiloh (F), J. Robbins (RB), M. Greene (T) R. Hay (WS-1), T. Kakunaga (KD) and Mr. R. Trimmer of NCI (RJH 4, DW Sr, BH, PC 109).

EXAMPLE 1

Protocol for Quantifying $G_2$ Chromosomal Radiosensitivity of Fibroblasts. The following protocol is exemplary of the present process and is performed in parallel with test samples and control cultures.

Log phase skin fibroblasts adapted to a glass substrate are prepared by:

(a) Transferring cells to glass flasks with silicone stoppers at least 11 days before assaying (NOTE: All glassware for cultures should be scrupulously cleaned prior to use to ensure best results.)

(b) Renewing the culture medium on days 8 and 6 before assay. One medium found suitable for use is Dulbecco's Modified Eagle's media ("DMEM" - Morton, H.C. "A survey of commercially available tissue culture media", In Vitro 6(2):89–108 (1970), at 92–93) a chemical nutrient solution designed for growing cells in culture, with 4.5 g/l glucose and 10% fetal bovine serum (MA Bioproducts, Walkersville, Md. and Flow Laboratories, McLean, VA, respectively).

(c) Subculturing the fibroblasts on day 4 before assay.

(d) Renewing the culture medium 24 hours before assay. Cultures should be sub-confluent for assay.

2. To prepare replicate cultures for irradiation:

(a) Rinse culture with ethylene diamine tetraacetic acid (versene 1:5000, MA Bioproducts) for about 30 seconds.

(b) Withdraw versene and add just enough trypsin to cover cell monolayer. It is suggested that the trypsin (e.g. 0.1% - Worthington 3x crystallized) be prepared just prior to use from a frozen stock kept in $Ca++$, $Mg++$-free culture medium without serum and diluted with versene just prior to use.

(c) Gently tap flask to detach cells, then inactivate trypsin by adding a small aliquot of culture medium. Bottles of medium and serum at the commercial source of preparation, during shipping, storage and use, as well as cultures in the medium, should at all times be protected from light of wavelength <500 nm to avoid adversely affecting the assay results. Suggested means include aluminum foil wraps, yellow bags, gold or red room lights, and appropriate light filters for microscope observation.

(d) Adjust cell suspension to about $0.5-1\times10^5$ cells/2 ml medium. For reproducibility, inoculum size should be adjusted to obtain equivalent cell densities (e.g. 75% confluence) at the time of irradiation 48 hours later.

(e) Inoculate cell suspensions into glass culture flasks or vessels containing a clean glass coverslip or glass slide. For best results, equilibrate gas phase with humidified 10% $CO_2$ in air, seal with #0 silicone stopper and incubate at 37° C. It should be noted that maintenance of physiologic pH is necessary to avoid adversely affecting test results.

(f) Renew medium 24 hours before irradiation.

3. To irradiate cultures:

(a) After 48 hours incubation, examine cultures microscopically, preferably at 37° C., looking specifically for condition of cells and presence of metaphase cells.

(b) Add 0.1 µg/ml Colcemid (Gibco, Grand Island, N.Y.) to a volume of medium, sparge with 10% $CO_2$ in air and warm to 37° C.

(c) Expose cultures to 0, 25, 50, or 100 Roentgen. The results in Tables 1 and 2 were achieved using 250 kV potential x-ray tubes operated at 235 kV, 15 mA, with 0.25 mm Cu and 0.55 mm Al filters (half value layer 0.9 mm Cu) at a dose rate of 126 R/min. at 54 cm target distance. Cells should be returned to 37° C. as quickly as possible since a drop in temperature affects test results. Alternatively, cultures may be exposed at 37° C. to cool-white fluorescent light from 2 desk lamps (8W/$M^2$ at the growth surface) for about 2 hours.

(d) To allow cells in mitosis during x-irradiation to complete division, allow approximately 30 minutes before culture medium renewal. Withdraw irradiated medium and add to each culture about 2 ml of prewarmed, pregassed nonirradiated medium containing about 0.1 μg/ml Colcemid. See, FIG. 6. With light exposure, it is not necessary to renew the culture medium.

4. To process cells for chromosome analysis:

(a) After about 1 hour incubation with Colcemid (N-desacetyl-N-methylcochicine) at 37° C., decant medium, invert culture and gently add to roof of culture vessel 2 to 5 ml 0.53% KCl in distilled $H_2O$ prewarmed to 37° C. Return culture to original position and incubate for 15 minutes at 37° C. Alternatively, cells can be removed with trypsin and processed in suspension as described later for lymphocytes.

(b) Prepare fixative at room temperature just before use. A suitable fixative comprises 1 part glacial acetic acid:3parts absolute methanol.

(c) Decant KCl solution, invert culture and gently add to roof of the culture vessel 2 to 5 ml fixative. Return culture to original position and fix for about 30 minutes at room temperature.

(d) Remove coverslip or slide from vessel, air-dry at an angle and, preferably, store for at least 24 hours before staining.

(e) Stain coverslip or slide about 4 minutes with 2% aqueous Giemsa (Harleco, Gibbstown, NJ). Rinse in tap water, air-dry, dip in xylene and mount on a clean slide with a mounting medium.

5. To quantify $G_2$ chromosomal radiosensitivity:

(a) Scan samples for complete well-spread metaphase cells.

(b) Score each metaphase cell for number of chromatid breaks (showing distinct dislocation and misalignment of the chromatid fragment), chromatid gaps (or achromatic lesions longer than the width of the chromatid, showing apparent chromatid discontinuity, but no dislocation), and other chromosomal abnormalities as experimental objectives dictate.

Protocol for lymphocyte culture.

1. In a T-25 flask prepare 35 ml of medium comprising RPMI 1640 (Microbiological Associates, Walkersville, Md.) 15% FBS +0.29 mg/ml additional glutamine. Add 10 μ/ml heparin (GIBCO, No. 165-5680). Gas well in $CO_2$ incubator or purge with 10% $CO_2$ in air.

2. Keep refrigerated and wrapped in foil until blood is added. Add 3.5 ml freshly collected whole blood. Add 1% PHA stock (0.40 ml Wellcome cat. no. HA15, reagent grade, 1 mg/ml). Cap tightly and mix by swirling flask. Gas well again.

3. Incubate upright (surface-volume ratio may be important) at 37° C. for 72 hours. We get a low mitotic index at 48 hours.

4. For experimental treatment, mix contents of T25 well, dispense equally to 7 glass 15 ml centigrade tubes. Spin at 37° C., 900 rpm, 9 min. (150×g) or until red cells are pelleted and medium is clear and amber colored. (Lower rpm and less time are preferable.)

5. Remove medium almost to pellet; don't disturb pellet if possible. X-ray 100 R with tubes lying at a 45 angle or less, preferably on a large flat flask containing warm (37° C.) water.

6. Return tubes to 37° C., suspend cells in pellet in 5 ml fresh RPMI 1640+15% FBS. Incubate for 0.5, 1.5 or 2.5 hours at 37° C. Colcemid (0.1μg/ml) is added immediately to the ½ hour cultures for ½ hour. Colcemid is added to others 1 hour before takeoff (see FIG. 7). Unirradiated controls can be harvested last.

7. Takeoff procedure: spin tubes at 37° C., 900 rpm, 9 minutes. Remove medium and add 10 ml 37° 0.53% KCl in distilled $H_2O$ (0.53 g/100 ml).

8. Mix and incubate 20 minutes at 37°, spin 37°, 900 rpm, 9 minutes, remove clear, red supernatant down to approximately 0.75 ml. Mix with pellet.

9. Immediately add 10 ml freshly prepared cold glacial acetic acid (1 part) +methanol (3 parts) preferably at 4.C., using glass pipets only. It is important to add only a drop or two initially, mix well (suspension will blacken immediately), then add a few more drops, mix well again, until cells and hemoglobin are well dispersed. Avoid vigorous pipetting.

10. Maintain at 4° C.(in ice bath) 30 minutes, spin (4° C.), withdraw old fixative and add a drop or two of fresh fixative, resuspend pellet, bring up to 5 ml. Store in refrigerator, preferably at least overnight for best metaphase spreads.

11. Metaphase preparations: spin tubes at 4° C., remove old fixative, add 0.25 to 1.0 ml fresh fixative, drop onto dry, room temperature slides preferably from a height of about 6 feet. (Low relative humidity may require the use of steam or cold, wet slides to produce good metaphase spreads). Dry overnight (room temperature only).

12. Stain slides for 4 minutes in Wright-Giemssa (Harleco, Azure B) (3 parts)+distilled $H_2O$ (125 parts), at pH 6.8-7.0, adjusted with Fisher pH 7 buffer. Air dry overnight at room temperature only.

13. For permanent preparations, add mounting medium and coverslip, and dry at room temperature. (Higher temperatures may affect stain and chromosome appearance).

Statistical Calculations

In all cases, statistical comparisons of data are based on the t-test after taking a square root transformation of the aberration frequencies (Snedecor et al. *Statistical Methods*, pp. 208-213 Ames, IA:University Press (1980)).

DESCRIPTION OF THE DRAWINGS

FIG. 5: Effect of bacterial contamination on response of cells to x-irradiation during $G_2$ phase. Each determination is based on 4 cultures with a total of 50 to 100 metaphase cells examined per variable. Bar=1 standard error of the mean.

FIG. 6: Exemplary post-irradiation procedure for skin fibroblasts.

FIG. 7: Exemplary post-irradiation procedure for blood lymphocytes.

Tables 1–2: Comparative response to x-irradiation (100 R) during $G_2$ of skin fibroblasts from clinically normal individuals with those from individuals with hereditary neoplasms or familial cancers.

Tables 1 and 2 compare cell response to x-irradiation (100 R) during $G_2$ of skin fibroblasts from clinically normal individuals and those from individuals with cancer-prone genetic disorders, hereditary neoplasms or familial cancers. In these results, the effects of the various noted process parameters are shown and discussed.

In Table 1, the results of the Series I tests are tabulated. In Series I, one lot of serum was used throughout, and each culture was individually gassed to adjust pH at the post-irradiation medium renewal step. In Series II tests, two new lots of serum were used. Because individual gassing of cultures after irradiation was time-consuming, this step was omitted, however, the medium added to the cultures post-irradiation had previously been equilibrated with humidified 10% $CO_2$ in air to adjust the pH. The two series are listed separately because of these differences in experimental conditions.

Non-irradiated cells in both series, whether of normal or cancer-prone origin, had a negligible background of spontaneous chromatid breaks and gaps. In both series, the frequencies of chromatid breaks and gaps after irradiation were significantly higher in skin fibroblasts from cancer-prone individuals as a group than in fibroblasts from normal controls. In Series I, each cancer-prone cell line had significantly more gaps than normal except the XP variant and the XP-A cells. In Series II, every cancer-prone cell line had significantly more gaps than normal except F218.

In Series I, skin fibroblasts from normal individuals <1 year of age, i.e., fetal and 3-day foreskin, differed in response from those >1 year of age, showing significantly more chromatid damage. In Series II, skin fibroblasts from one 3 month-old infant also showed higher radiation-induced damage. The enhanced radiation-induced damage persisting in fetal and infant cells may reflect developmental processes in which genes for the normal response are not yet expressed. No significant difference in response with respect to sex or age was apparent in cells from normal individuals >1 year of age in either Series I or II. However, cells of two lines in Series II, F664 and 3216T, from clinically normal donors responded like those from cancer-prone individuals, while cells from the XP-A individuals responded like those from normal individuals. The extent of chromatid damage in both normal and cancer-prone cells was significantly higher in Series II than in Series I. In addition, the ratio of chromatid gaps to breaks was 3- to 4-fold higher in Series I than in Series II.

Figure 1:
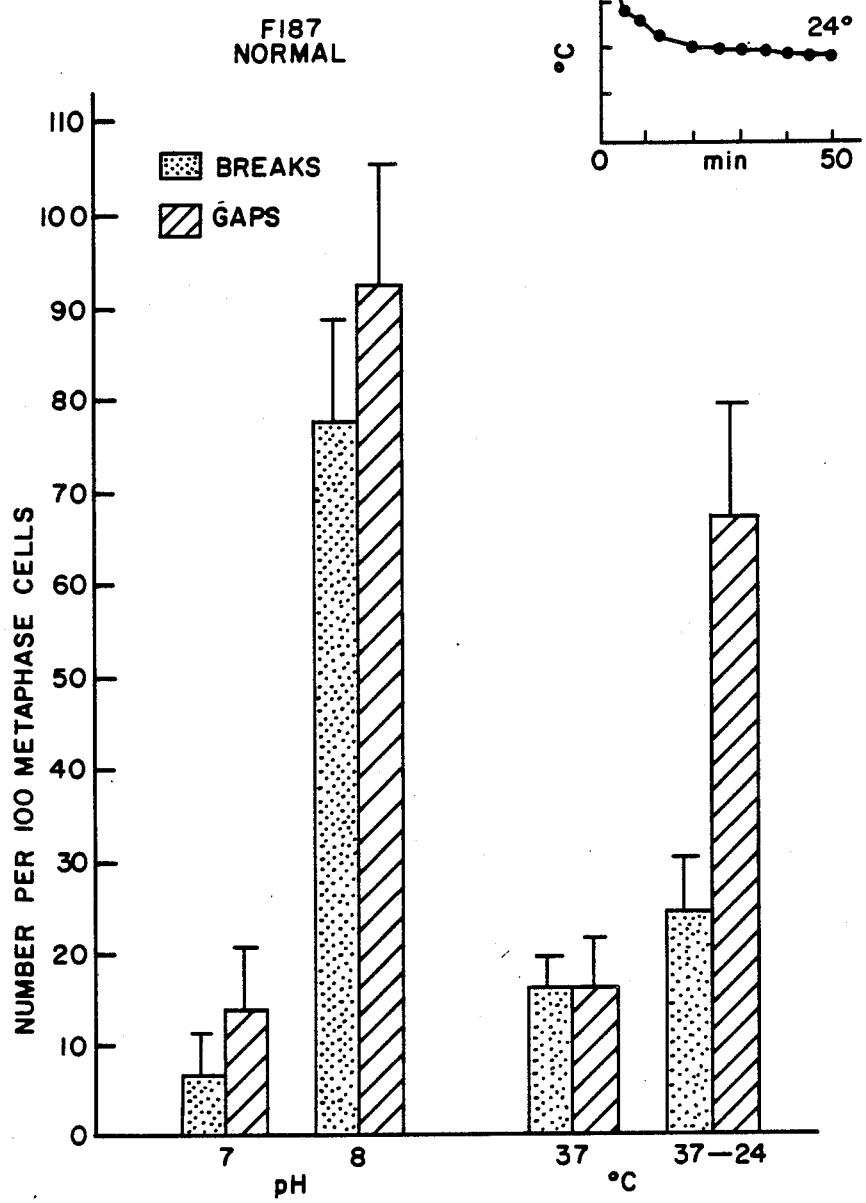
FIG. 1: Effect of pH and temperature on frequency of chromatid breaks and gaps after $G_2$ phase x-irradiation (100 R). Four cultures per variable were each inoculated with 7×$10^4$ skin fibroblasts of line F187 from a clinically normal individual. Each determination was based on analysis of 100 metaphase cells with the exception of 29 at pH 7 and 75 at low temperature. Unirradiated control cells at either pH showed no chromatid breaks or gaps. Bar=1 standard error of the mean.

Factors Affecting Assay Results pH and temperature. Increasing pH from 7 to 8, or reducing temperature from 37° C. to room temperature, 24° C., during the repair period following $G_2$ phase x-irradiation has been found to affect the extent of damage in metaphase cells collected by Colcemid from 0.5 to 2 hours after irradiation. The numbers of chromatid breaks and gaps were 6.7- to 11-fold higher in cultures maintained at the nonphysiologic pH of 8. Similarly, chromatid damage was 1.5 to 4-fold higher in cultures transferred to room temperature (see, FIG. 1). Therefore, precise control of pH and temperature is urged to prevent false positive results. The more rigid control of pH by gas phase equilibration of individual cultures in Series I compared with Series II (Tables 1 and 2) may account, in part, for the lower frequencies of chromatid damage seen in Series I.

Figure 2:
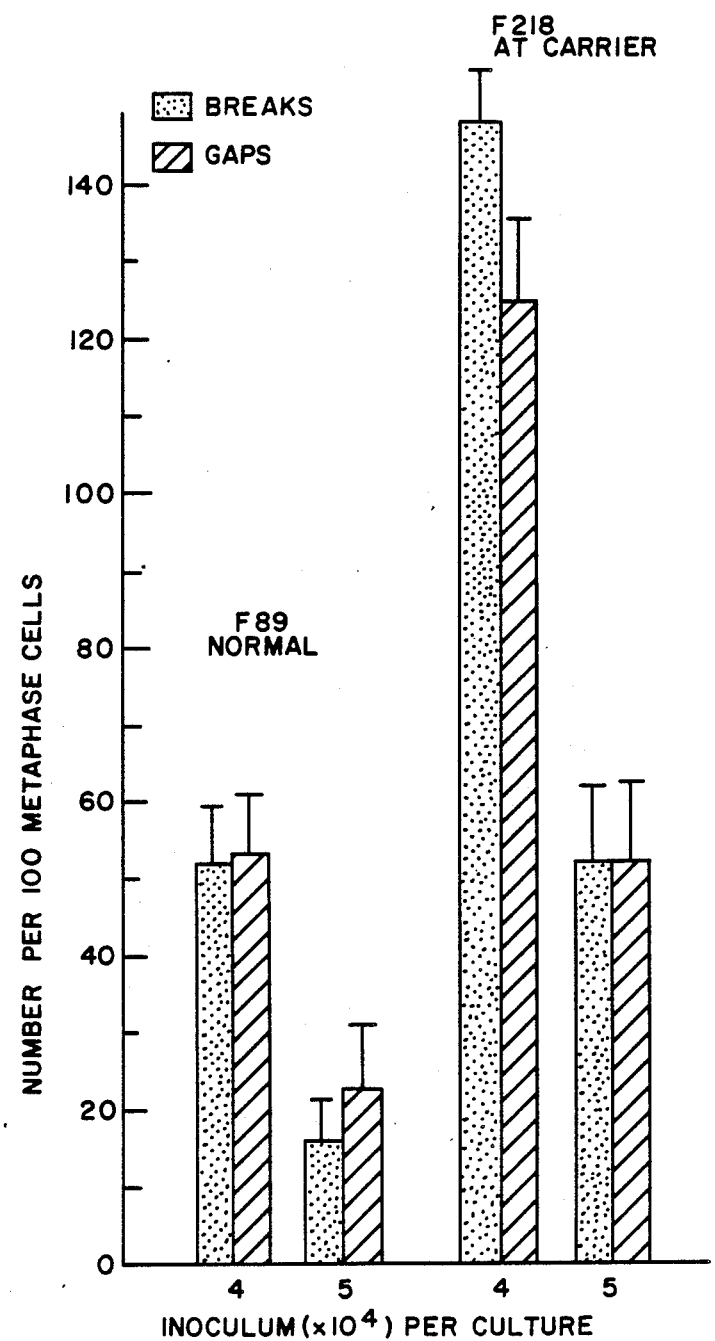
FIG. 2: Effect of cell density on frequency of chromatid breaks and gaps in normal skin fibroblasts and those from an ataxia telangiectasia heterozygote. Metaphase cells were collected 0.5 to 2 hours after $G_2$ phase x-irradiation (100 R). The average number of cells per coverslip (9×50 mm) at the time of x-irradiation, 48 hours after inoculation, was as follows: F89, 2.1 and 5.0 ×10⁴; F218, 2.8 and 4.9×10⁴. Each determination is based on 4 cultures with a total of 44 to 100 metaphase cells examined per variable. Bar=1 standard error of the mean.

Cell density. Confluent cultures, especially of anchorage-dependent normal cells, do not provide sufficient numbers of mitotic cells for analysis. On the other hand, inoculum sizes lower than 5×10⁴ cells per culture frequently yield variable results. The effect of low cell density on chromatid damage after $G_2$ phase x-irradiation (100 R) was tested on normal cells (F89) and cells from a heterozygote cancer-prone carrier of the gene for ataxia telangiectasia (A-T) (F218) (see, FIG. 2). At the low inoculum sizes, not all cells had attached and/or divided by 48 hours after inoculation (see legend, FIG. 2). Furthermore, the numbers of chromatid breaks and gaps in metaphase cells collected by Colcemid 0.5 to 2 hours after irradiation were 2.4 to 3.3-fold higher at the low cell densities of both cell lines than at the high cell density. Therefore, an inoculum size >5×10⁴ cells per culture may be necessary to prevent false positive results. The cell number at the time of irradiation appears to be significant too. For this reason, cells were pre-adapted to a glass substrate because cells transferred from plastic to glass may not attach and this loss will decrease cell density at the time of irradiation. Glass rather than plastic coverslips were used as a growth substrate since most plastic formulations cannot withstand the solutions required for chromosome processing and mounting.

Commercial source of medium and medium renewal. Although all media and cultures employed herein were shielded from light of wavelength <500nm, commercial lots of medium or serum may not have been so shielded prior to delivery, and may therefore have developed toxic photoproducts such as hydrogen peroxide that gives rise to clastogenic free hydroxyl radicals (.OH); these in turn can increase background spontaneous frequencies of chromatid damage. Furthermore, the serum may have other chemical contaminants or biologic components that are toxic to the cells which would reduce cell viability and would affect chromosomes or repair of radiation-induced damage.

Figure 3:
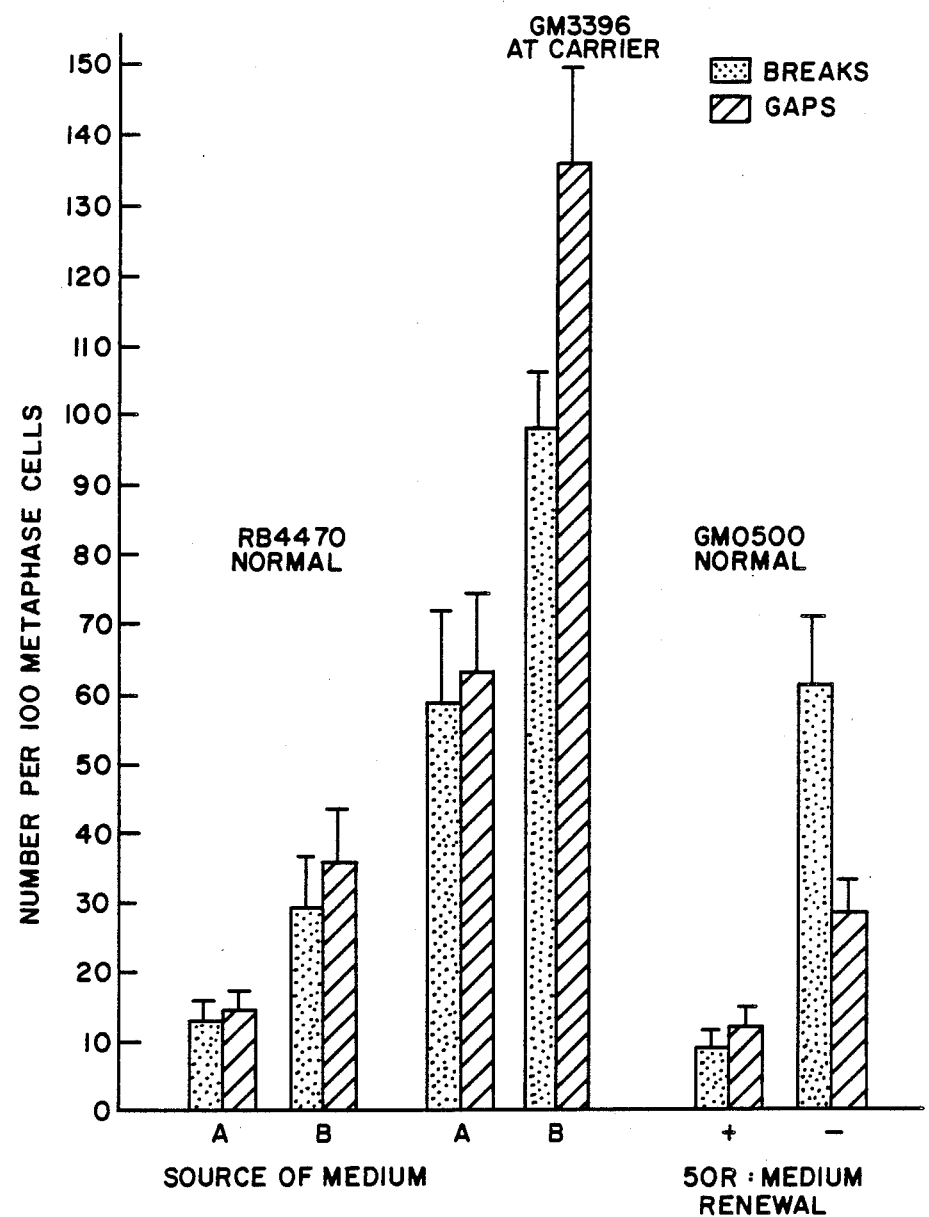
FIG. 3: Effect of commercial source of medium and medium renewal on chromatid damage after $G_2$ x-irradiation (100 R) in skin fibroblasts. Each determination is based on 4 cultures with a total of 100 to 200 metaphase cells examined per variable. Unirradiated cells (breaks/gaps per 100 metaphases) RB 4470: A medium, 0/1.2; B medium, 4.3/2.9. GM 3396: A medium, 1.8/1.8; B medium 3/5. Bar=1 standard error of the mean.

To demonstrate this, DMEM with 10% fetal bovine serum was obtained from two different commercial sources designated A and B (see, FIG. 3). Skin fibroblasts from a clinically normal individual, line RB 4470, and from an A-T heterozygote, GM 3396, were inoculated at $5 \times 10^4$ cells per culture into the two lots of medium. Cells cultured in medium B, compared with those in medium A, maintained 1.5 to 2.2-fold more induced chromatid breaks and gaps in cells entering metaphase 0.5 to 2 hours after x-irradiation (100 R). The unirradiated cells in medium B also had more chromatid damage.

In a second experiment, the culture medium was not renewed after x-irradiation (50 R) (FIG. 3). The cells in the irradiated medium collected 0.5 to 2 hours after irradiation showed a 7- and a 2.4-fold higher frequency of chromatid breaks and gaps, respectively. Thus, maintaining cells for long periods in irradiated medium may induce additional chromatid damage, presumably from generated $H_2O_2$, derivative free radicals or other radiation products. For this reason, the culture medium should be renewed after x-irradiation of cells.

Figure 4:
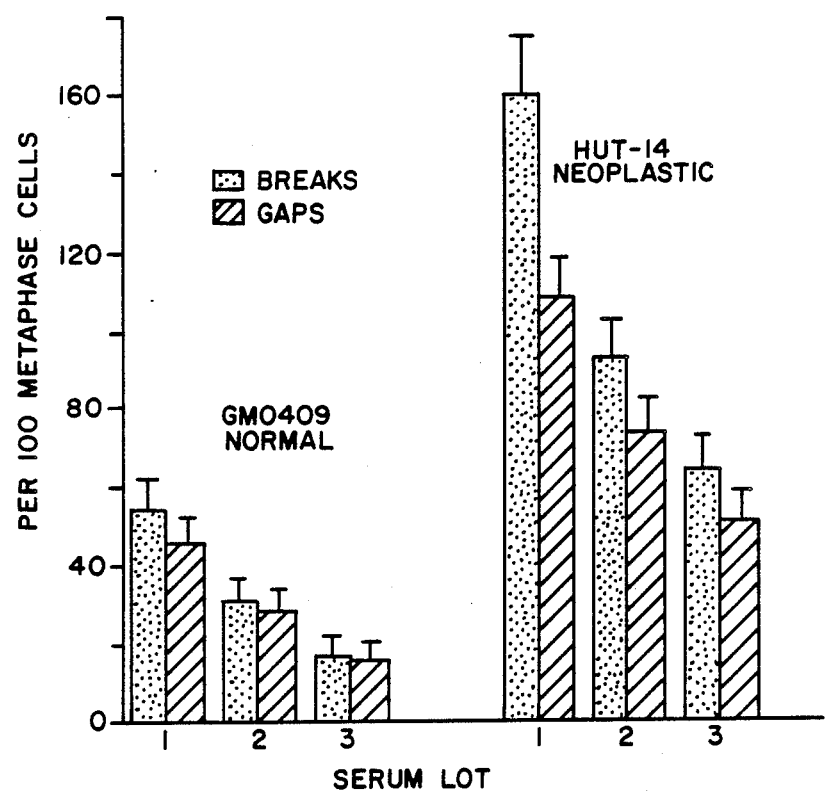
FIG. 4: Effect of commercial serum lot on chromatid damage in skin fibroblasts after $G_2$ x-irradiation (100 R). Each determination is based on 4 cultures with a total of 100 metaphase cells examined per variable. Bar=1 standard error of the mean.

Different commercial lots of serum were also found to affect cellular responses (FIG. 4). Therefore, the lots should be prescreened for minimal radiation-induced chromatid damage using test cells and controlled as much as possible with respect to light exposure in order to obtain reproducible results. In fact, the different lots of serum used in Series I and II (Tables 1 and 2) may account in large part for the different results obtained.

Bacterial contamination. In various experiments, certain cultures were found to be contaminated by a persistent low level of bacteria. These cultures showed a higher than normal frequency of radiation-induced damage. The data of FIG. 5 illustrate the erratic false positive results that may occur if cultures are contaminated. Microbial contamination, through nutrient depletion or metabolic products, may increase the susceptibility of mammalian cells to radiation damage, hinder repair processes or even protect against radiation damage. Since antibiotics can mask inapparent microbial infections, cultures should be carried without antibiotics or be maintained for at least several weeks in antibiotic-free medium before use. Furthermore, all cultures should be tested and found negative for mycoplasma or other contamination to avoid erroneous results.

The summary of these test results, as tabulated in Tables 1 and 2, show a clear difference in response between skin fibroblasts from clinically normal individuals and those with genetic disorders predisposing to a high risk of cancer, including healthy carriers of the HCMM/DNS gene or the A-T gene (A-T heterozygoteos). The frequencies of chromatid breaks and gaps in metaphase cells collected during the post-irradiation period were several fold higher in the cells from cancer-prone individuals than in those from normal controls. This difference was apparent even under the diverse culture conditions (varied process parameters) which affect the absolute number of aberrations shown in FIGS. 2 and 3.

Similar results have been noted for skin fibroblasts exposed to fluorescent light (effective wavelength 405 nm in the visible range) rather than x-rays. Thus, both forms of radiation are contemplated for use in the present process. Skin fibroblasts from cancer-prone donors harvested several hours after light exposure, such that they were in $G_1$ or S phase at the time of exposure, did not differ from normal cells in extent of chromatid damage, thus the difference in response between normal and cancer-prone cells appears to be limited to cells irradiated during $G_2$ phase.

The enhanced frequencies of chromatid breaks and gaps in the cancer-prone cells do not result from greater susceptibility to initial DNA damage by radiation nor are they due to different rates of progression through $G_2$ and prophase. Furthermore, the enhanced response of cancer-prone cells is seen in skin fibroblasts irradiated with light and in lymphoblasts irradiated with x-rays under conditions where there is minimal radiation-induced mitotic delay. These observations support the concept that the abnormal response of cancer-prone cells does not result from a differential effect of irradiation on progression of cells through $G_2$ and prophase into metaphase.

The enhanced chromatid damage seen in the post-irradiation period could result from a $G_2$ phase deficiency(ies) in repair of the radiation-induced DNA damage leading to chromatid breaks and gaps at the subsequent metaphase. As noted previously, XP group A cells, like normal cells, do not show the enhanced chromatid damage after $G_2$ x-irradiation (Table 1); similar results have also been reported with respect to fluorescent light exposure. These cells are essentially devoid of endonuclease incision of DNA, an early step in excision repair. The failure to obtain the enhanced frequency of radiation-induced chromatid damage in XP-A cells suggests that endonucleolytic incision of DNA is requisite for chromatid gap and/or break formation and that incomplete excision repair may be important in the development of these chromatid aberrations. Incomplete excision repair of DNA damage would result in DNA single-strand breaks. Single-strand breaks, in turn, can lead to double-strand breaks manifest at metaphase as chromatid breaks.

It has been shown previously that the addition of a low concentration of $\beta$-cytosine arabinoside (ara-C., 50 $\mu$M) to normal cells following irradiation enhances the frequency of chromatid damage to the level observed in the irradiated cancer-prone cells. However, ara-C, which inhibits the polymerase step in excision repair, has no effect on chromatid damage in x-irradiated XP-A cells. These observations provide evidence that enhanced chromatid aberrations can result from indirect or secondary DNA strand breaks and support the concept that they represent sites of incomplete repair of DNA damage by deficient or unbalanced excision repair processes during $G_2$ phase. The stringent pH, temperature and cell density requirements of the present assay indicate that the repair processes are sensitive to these conditions.

TABLE 1

APPENDIX A Series

| Normal donor | Age (yrs) Sex (F, M) | Chromatid damage Av. per 100 metaphases[a] x-irradiation (1Gy) Breaks | Gaps | Cancer-prone donor or cancer patient | Clinical Status | Chromatid damage Av. per 100 metaphases x-irradiation (1Gy) Breaks | Gaps |
|---|---|---|---|---|---|---|---|
| Age >1 yr. | | | | | Ataxia telangiectasia | | |
| CRL 1222 | 8 M | 1 | 13 | GM 3487 | Homozygote | 34 | 119 |
| GM 0500 | 10 M | 0 | 6 | GM 3395 | Homozygote | 39 | 111 |
| KD | 31 F | 2 | 5 | GM 2797 | Heterozygote | 20 | 69 |
| CRL 1224 | 40 F | 5 | 10 | GM 3396 | Heterozygote | 22 | 71 |
| CRL 1221 | 40 M | 1 | 10 | GM 3397 | Heterozygote | 21 | 67 |
| CRL 1191 | 45 M | 2 | 6 | GM 3489 | Heterozygote | 19 | 71 |
| CRL 1232 | 58 M | 1 | 9 | GM 3488 | Heterozygote | 29 | 91 |
| CRL 1188 | 63 F | 1 | 9 | GM 2548 | Bloom Syndrome | 19 | 33 |
| RJH 4 | 66 M | 1 | 8 | | Fanconi anemia | 12 | 34[b] |
| GM 1680 | 71 F | 1 | 5 | | Xeroderma pigmentosum | | |
| GM 0731 | 96 M | 2 | 8 | CRL 1223 | Group A | 0 | 4 |
| | Av. | 1.6 | 8.0 | CRL 1261 | Group A | 1 | 0 |
| | Range | (0–5) | (5–13) | CRL 1158 | Group C | 8 | 45 |
| | Non-irradiated controls | | | | | | |
| | Av. | 0.7 | 0.6 | GM 0709 | Group C | 20 | 72 |
| | Range | (0–2) | (0–3) | GM 2415 | Group E | 2 | 46 |
| | | | | CRL 1162 | Varient | 10 | 12 |
| | | | | 3061 T | Familial dysplastic nevus syndrome (DNS) | 88 | 194 |
| Age >1 yr. | | | | PC 109 | Familial polyposis | 9 | 47 |
| IMR 90[c] | Fetal | 67 | 21 | DW Sr | Gardner syndrome | 10 | 29 |
| WS-1 | " | 44 | 84 | BH | " | 5 | 44 |
| NCTC 10427[d] | 3 days M | 16 | 50 | 2809 T | Hereditary cutaneous malignant melanoma/DNS | 64 | 214 |
| NCTC 10458[d] | " | 24 | 43 | 2991 T | Hereditary cutaneous malignant melanoma/DNS | 70 | 205 |
| NCTC 10462[d] | " | 10 | 12 | 3072 T | Hereditary cutaneous malignant melanoma/DNS | 5 | 29 |
| | | | | 3248 T | Hereditary cutaneous malignant melanoma/DNS | 8 | 39 |
| | Av. | 32.5 | 42.0 | 3190 T | Hereditary cutaneous malignant melanoma/DNS | 14 | 44 |
| | Range | (16–67) | (12–84) | 3012 T | Hereditary cutaneous malignant melanoma/DNS | 15 | 63 |
| | Non-irradiated controls | | | | | | |
| | Av. | 0.3 | 0.2 | Ag 3000 | Cancer family | 11 | 53 |
| | Range | (0–1) | (0–1) | AG 3499 | " | 19 | 55 |
| | | | | Ag 3302 | " | 14 | 46 |
| | | | | AG 3308 | " | 19 | 52 |
| | | | | AG 2655 | " | 13 | 57 |
| | | | | AG 3778 | " | 22 | 81 |
| | | | | | Av. | 20.7 | 67.6 |
| | | | | | Range | (2–70) | (0–214) |
| | | | | | Non-irradiated controls | | |
| | | | | | Av. | 0.9 | 1.4 |
| | | | | | Range | (0–3) | (0–6) |

[a]Values represent induced damage, i.e., irradiated (1Gy) minus non-irradiated.
[b]0.5 Gy rather than 1 Gy.
[c]Fetal lung origin.
[d]Foreskin origin.

TABLE 2

APPENDIX B Series II

| Normal donor | Age (yrs) Sex (F, M) | Chromatid damage Av. per 100 metaphases[a] x-irradiation (1Gy) Breaks | Gaps | Cancer-prone donor or cancer patient | Clinical Status | Chromatid damage Av. per 100 metaphases[a] x-irradiation (1Gy) Breaks | Gaps |
|---|---|---|---|---|---|---|---|
| Age >1 yr. | | | | | Ataxia telangiectasia | | |
| GM 5758 | 1.3 M | 20 | 20 | | Homozygotes | | |
| GM 5659 | 1.3 M | 20 | 20 | F 184 | Homozygotes | 145 | 120 |
| AG 7095 | 2 M | 12 | 14 | F 320 | " | 306 | 202 |
| GM 5565 | 3 M | 18 | 16 | F 112 | " | 124 | 105 |
| GM 0409 | 7 M | 19 | 19 | F 58 | Heterozygotes | 116 | 93 |
| F 196 | 10 M | 11 | 13 | F 26 | " | 88 | 72 |
| GM 1652 | 11 F | 13 | 18 | F 30 | " | 163 | 158 |
| GM 2987 | 19 M | 18 | 18 | F 57 | " | 89 | 74 |
| GM 3377 | 19 M | 18 | 18 | F 218 | " | 48 | 49 |
| F 187 | 24 M | 17 | 17 | F321 | " | 141 | 111 |
| GM 3652 | 24 M | 20 | 19 | | Xeroderma pigmentosum | | |

TABLE 2-continued
APPENDIX B
Series II

| Normal donor | Age (yrs) Sex (F, M) | Chromatid damage Av. per 100 metaphases[a] x-irradiation (1Gy) | | Cancer-prone donor or cancer patient | Clinical Status | Chromatid damage Av. per 100 metaphases[a] x-irradiation (1Gy) | |
|---|---|---|---|---|---|---|---|
| | | Breaks | Gaps | | | Breaks | Gaps |
| KD | 31 F | 18 | 19 | CRL 1170 | Group C | 38 | 74 |
| F 89 | 32 M | 20 | 22 | 3669 T | Dysplastic nevus syndrome (DNS) | 113 | 101 |
| F 664 | 32 M | 112 | 92 | | | | |
| 2585 T | 32 F | 18 | 20 | 3668 T | Dysplastic nevus syndrome (DNS) | 58 | 69 |
| 3216 T | 37 M | 61 | 57 | 3672 T | Dysplastic nevus syndrome (DNS) | 134 | 124 |
| 3054 T | 40 F | 20 | 18 | 3218 T | " | 114 | 107 |
| 2602 T | 41 M | 18 | 18 | 3695 T | " | 52 | 151 |
| 3185 T | 44 F | 16 | 18 | 3169 T | " | 76 | 118 |
| 3694 T | 45 T | 6 | 10 | 3666 T | Hereditary cutaneous malignant melanoma with DNS | 216 | 199 |
| RB 4470 | 49 M | 13 | 14 | 3359 T | Hereditary cutaneous malignant melanoma with DNS | 44 | 124 |
| 3047 T | 52 M | 19 | 19 | 2807 T | Hereditary cutaneous malignant melanoma with DNS | 136 | 122 |
| 2589 T | 53 F | 19 | 17 | 3676 T | Hereditary cutaneous malignant melanoma with DNS | 76 | 194 |
| 2995 T | 55 F | 12 | 16 | 3030 T | Hereditary cutaneous malignant melanoma with DNS | 160 | 167 |
| RB 4087 | 55 F | 18 | 21 | | Retinoblastoma[b] | | |
| 2583 T | 57 F | 18 | 18 | GM 5877 | Bilateral | 236 | 227 |
| 3677 T | 62 F | 7 | 11 | GM 1142 | " | 256 | 250 |
| 3673 | 85 F | 16 | 14 | GM 4250 | " | 255 | 223 |
| | Av. | 21.3 | 21.3 | GM 2971 | " | 203 | 191 |
| | Range | (6–112) | (10–92) | GM 1879 | " | 49 | 51 |
| | Non-irradiated controls | | | | | | |
| | Av. | 0.3 | 0.4 | GM 6418 | " | 171 | 160 |
| | Range | (0–2) | (0–2) | GM 6419 | " | 51 | 71 |
| Age <1 yr | | | | | | | |
| | | | | GM 1880 | Unilateral, familial | 87 | 95 |
| | | | | GM 2718 | Unilateral Wilms' tumor | 203 | 207 |
| | | | | GM 3118 | Bilateral | 58 | 74 |
| | | | | GM 3808 | AGR triad | 55 | 58 |
| | | | | 3671 T | Cancer family | 34 | 64 |
| | | | | | Av. | 124.1 | 128.0 |
| | | | | | Range | (34–306) | (49–250) |
| | | | | | Non-irradiated controls | | |
| | | | | | Av. | 1.0 | 1.1 |
| | | | | | Range | (0–4) | (0–5) |

[a]Values represent induced damage, i.e., irradiated (1Gy) minus non-irradiated.
[b]All bilateral tumors are considered hereditary. The unilateral tumor of the donor of GM 2718 is multifocal and the peripheral lymphocytes have a partial deletion of the long arm of chr. 13, containing the retinoblastoma gene.

We claim:
1. A process for detecting genetic susceptibility to cancer comprising the steps of:
   (a) Irradiating a cell culture where $G_2$ cells are present with x-ray or fluorescent light, the cell culture being sub-confluent on the growth surface at the time of irradiation;
   (b) Incubating the irradiated cell culture to allow for DNA repair;
   (c) Renewing culture medium in the cell culture about 0.5 hours after irradiation;
   (d) Arresting cell division in the irradiated cell culture 0.5 to 2 hours after irradiation;
   (e) Determining the number of chromatid breaks and chromatid gaps in $G_2$ cells from the irradiated cell culture;
   (f) Analyzing the numerical results from step e to determine the frequency of chromatid breaks and chromatid gaps in the $G_2$ cells; and
   (g) Utilizing the analysis results of step (f) to detect genetic susceptibility to cancer.

2. The process of claim 1 wherein the cell culture comprises skin fibroblasts or peripheral blood lymphocytes.

3. The process of claim 1 wherein x-irradiation is performed at about 100 R.

4. The process of claim 1 wherein the fluorescent light irradiation is performed at about 8 W/M$^2$.

5. The process of claim 1, wherein steps (a)–(f) are performed both on normal or control $G_2$ cells and on unknown or test $G_2$ cells, and the frequencies of chromatid breaks and chromatid gaps are compared in step (g), wherein an increased frequency of chromatid breaks and chromatid gaps of said unknown or test $G_2$ cells as compared to said normal or control cells indicates genetic susceptibility to cancer.

6. The process of claim 1 wherein the cell culture is maintained at a physiologic pH prior to, during and immediately after irradiation.

7. The process of claim 1 wherein the cell culture and media are not exposed to light of wavelength <500 nm prior to, during or immediately after irradiation.

8. The process of claim 1 wherein the cell culture is maintained in antibiotic-free medium prior to irradiation for a period of time sufficient to verify the absence of microbial contamination.

9. The process of claim 1 wherein the cell culture is tests for mycoplasma or other biological contamination prior to irradiation.

10. The process of claim 1 wherein the sub-confluent cell culture covers approximately 75% of the growth surface area at the time of irradiation.

11. The process of claim 1 wherein the temperature of said cell culture is maintained at about 37° C.

* * * * *